United States Patent [19]

Goldfinger et al.

[11] Patent Number: 4,650,662
[45] Date of Patent: Mar. 17, 1987

[54] PORTABLE BLOOD TYPING APPARATUS AND METHOD

[75] Inventors: Dennis Goldfinger, Encino; Rock C. Hsi, Monterey Park, both of Calif.

[73] Assignee: Cedars-Sinai Medical Center, Los Angeles, Calif.

[21] Appl. No.: 670,882

[22] Filed: Nov. 13, 1984

[51] Int. Cl.[4] .................. G01N 33/48; C12Q 1/24; C12M 1/28; C12M 1/24

[52] U.S. Cl. .................... 424/11; 435/30; 435/294; 435/296; 435/810; 436/807; 422/58; 422/61; 422/100; 422/102; 141/8

[58] Field of Search ............ 424/11; 435/7, 30, 810, 435/287, 292, 293, 294, 296, 299, 300, 301; 436/807, 809, 520, 810; 206/219; 141/59, 65, 114, 8, 9, 311, 313; 422/58, 61, 73, 99, 100, 102

[56] References Cited

U.S. PATENT DOCUMENTS

| | | | |
|---|---|---|---|
| 2,595,493 | 5/1952 | Slaby et al. | 422/100 X |
| 3,122,124 | 2/1964 | Yocum | 422/58 X |
| 3,175,558 | 3/1965 | Caillouette et al. | 206/219 X |
| 3,410,635 | 11/1968 | Lockwood | 350/245 X |
| 3,433,712 | 3/1969 | Gerarde | 141/114 X |
| 3,572,552 | 3/1971 | Guinn | 422/100 X |
| 3,809,224 | 5/1974 | Greenwood | 206/219 |
| 3,919,053 | 11/1975 | Nazemi | 435/291 X |
| 4,067,313 | 1/1978 | Donnelly | 206/219 X |
| 4,167,955 | 9/1979 | Sharples | 141/9 X |

OTHER PUBLICATIONS

Thalhimer et al., J.A.M.A., vol. 149, Jul. 5, 1952, pp. 928-930.

*Primary Examiner*—Robert J. Warden
*Assistant Examiner*—Randall E. Deck
*Attorney, Agent, or Firm*—Lyon & Lyon

[57] ABSTRACT

A portable apparatus to enable rapid determination of an individual's ABO blood group and Rh blood type and a method of using such apparatus. The apparatus has a plurality of microtubes joined together which contain blood taken from an individual. The assembly of microtubes is connected during use to an assembly of reaction chambers containing blood typing reagents. The apparatus enables rapid visualization of the test reactions within the reaction chambers, and may be used in locations removed from a laboratory to determine the ABO blood group and Rh blood type of an individual.

18 Claims, 8 Drawing Figures

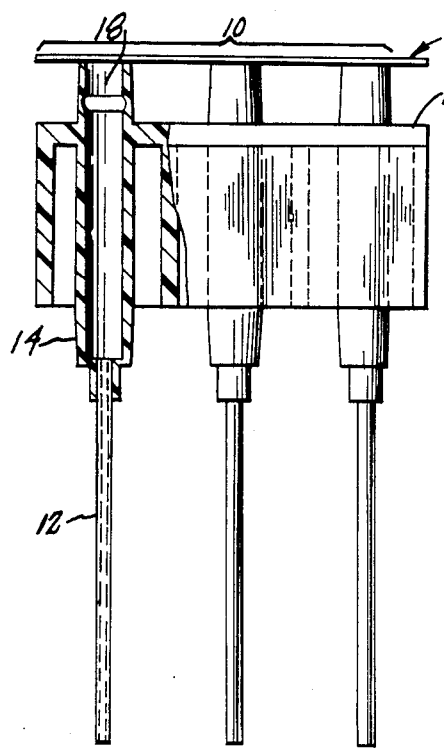
Fig_1.
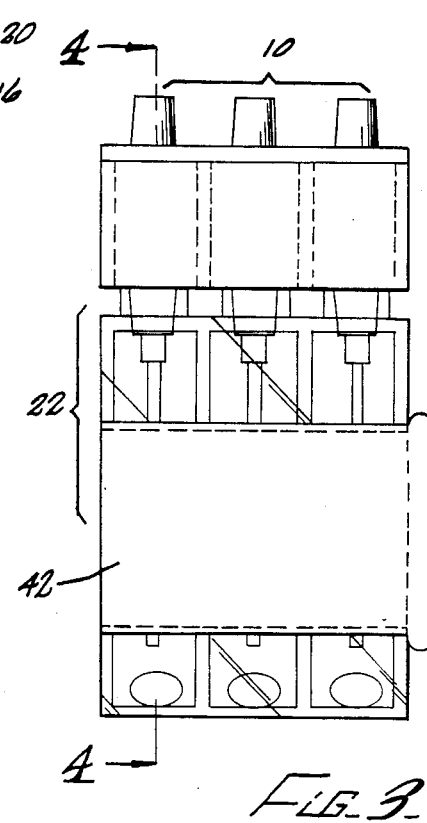
Fig_3.
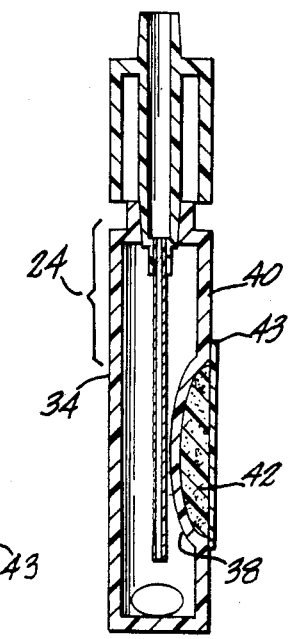
Fig_4.
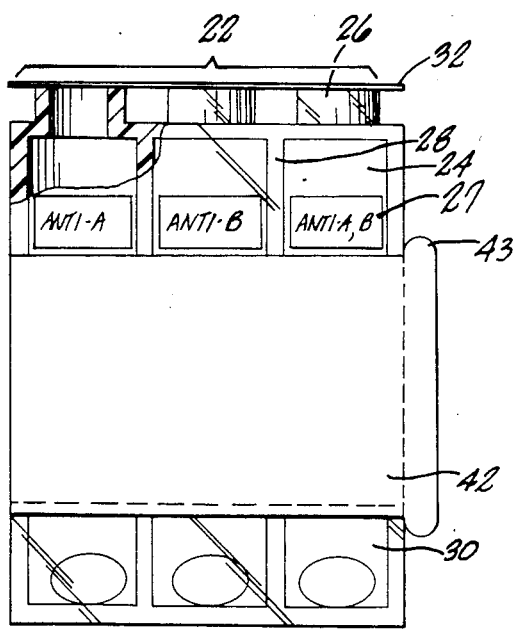
Fig_2.
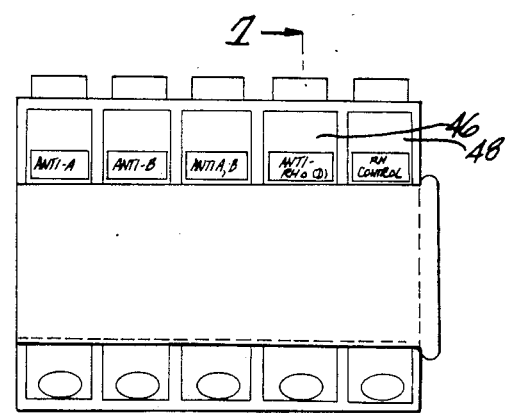
Fig_6.

PORTABLE BLOOD TYPING APPARATUS AND METHOD

BACKGROUND OF THE INVENTION

The field of the present invention is a portable apparatus for performing tests to identify the blood group and blood type of a patient according to the ABO and Rh blood type classification systems, and methods of using such apparatus.

The testing procedures for determining the ABO blood group and Rh type of an individual's blood are well known to those skilled in the art. The major blood groups are: type A, type B, type A,B and type O. These blood groups are determined by the antigens present on an individual's red blood cells. An individual with type A blood carries red blood cells with type A antigens. In addition, persons of a particular ABO type have antibodies in their blood plasma which react with the antigens that they lack. For example, individuals who are type A have antibodies to the B antigen. Type O individuals have both anti-A and anti-B antibodies. Typically blood typing involves both "forward" and "reverse" typing. Forward typing tests are performed on the person's red blood cells to determine which antigens are present. A confirmatory, reverse typing test to determine which antibodies are present is also usually performed in the laboratory on the individual's blood serum or plasma. (Technical Manual of the American Association of Blood Banks, 8th Ed. 1981, Washington, D.C.).

An additional important antigen is the Rho(D) antigen (hereinafter referred to as the Rh antigen). Determination of the presence or absence of the Rh antigen is known as determining the Rh type of a patient's blood. The presence or absence of the Rh antigen has significance during pregnancy. If a pregnant woman has Rh negative type blood, she may have developed Rh antibodies in a prior pregnancy. If her fetus has Rh positive type blood the mother could transfer Rh antibodies to the fetus, resulting in its death.

It is imperative in administering blood transfusions that the donor's blood have the same red blood cell antigens as those of the recipient patient, to prevent complications from introduction of incompatible blood. The introduction of incompatible blood into a recipient who has circulating antibodies may result in rapid destruction of the transfused red blood cells by the recipient's antibodies. This is known as actue hemolytic transfusion reaction. Acute hemolytic transfusion reactions are among the most feared of such blood transfusion complications. Such reactions may result in actue renal failure and may end in death. (*Fatalities From Blood Transfusion*, Byron A. Nyhre, JAMA, Vol. 224 No. 12, Pg. 1333, 1980). Most ABO incompatibility deaths involve blood group O recipients since they have the least number of possible compatible donors. (Schmidt, *Immunobiology Of The Erythrocyte*, Allan R. Liss, 1980, The Mortality From Incompatible Transfusion, pgs. 251-261, 1980.)

Acute hemolytic transfusion reactions account for the majority of deaths reported to the Food and Drug Administration each year by FDA-Registered Transfusion Services. Between the years 1976 and 1978, 22 deaths were reported to the FDA as a result of transfusion and were attributable to ABO blood group incompatibility which resulted in acute hemolytic transfusion reactions. Of these 22 deaths, the majority of these were because the wrong patient was transfused. (Schmidt, supra and Myhre, supra). In particular, a major cause of the transfusion of incompatible blood is clerical error. Clerical errors can occur at any point from the time of drawing a patient's blood, through the classification of that person's blood type. Such errors can also occur at the point where donor blood is transfused to that patient. Transfusions may occur at numerous locations in the hospital removed from the testing laboratory including the patient's bedside, operating room or the emergency room of the hospital. Clerical errors include mislabeling of the blood sample taken from the patient, drawing blood from the wrong patient, or transferring the wrong unit of blood to a patient.

The usual blood typing procedures are performed in a laboratory and test an individual's blood cells for the presence of the various antigens. Typically, a patient's blood sample is mixed together with a blood typing reagent. The mixture is then examined visually for an agglutination reaction. The blood typing reagents that are used in most typing tests to determine ABO blood group are anti-A, anti-B, and anti-A,B. The reagents used for Rh typing are anti-Rho (D) and an Rh control solution. These laboratory testing procedures require numerous devices and procedures including centrifugation, pipetting, and mixing of reagents in various containers. Typically several blood samples from different patients are run in blood testing apparatus simultaneously. It is obvious that clerical error that can lead to incorrent identification or interchanging of a blood sample can occur at any one of the many steps used in typing the blood in the laboratory setting.

There is available in the prior art individual plastic containers into which individual microtubes carrying a blood sample may be inserted. These containers hold a saline solution to dilute the blood sample. The containers are almost entirely made of soft plastic and are compressed by manual pressure to draw the blood into the container. The diluted blood sample is then transferred to an appropriate location, such as the laboratory, for blood counting. No blood typing reactions are carried out within such containers. There is also available in the prior art pre-packaged reagents within centrifugation apparatus for blood testing in a laboratory (U.S. Pat. Nos. 3,713,775 and 3,707,354) and predispensed reagents in separate containers for progressive mixing of the reagents with a single sample in a central chamber (U.S. Reissue Pat. No. Re. 29,725).

Presently, it is possible, to determine the ABO group of a patient's blood in a location other than a laboratory, for example a hospital bedroom, using individual testing materials. A drop of typing reagent, and a drop of the blood sample are placed on a glass slide. The reagent and blood sample are mixed together on the slide and the mixtures observed by the technician for agglutination. The disadvantages of this method are obvious; the procedure is inconvenient and tedious and can result in incorrect identification of the ABO blood group.

Additionally, a disadvantage of the techniques and apparatus for blood typing in the prior art is that a physician cannot perform an initial determination of a patient's ABO blood group and Rh blood type in his/her office because of the equipment and procedures required for laboratory blood testing. There is presently no easy and reliable means or method available for carrying out blood typing tests at any location removed from a laboratory.

SUMMARY OF THE INVENTION

The present invention is directed to a simple apparatus for determining a patient's blood type at a location removed from a laboratory, and a method for using such apparatus.

The present invention can assist in preventing acute hemolytic transfusion reactions and the resulting deaths, by providing confirmation of the potential recipient's ABO blood group at the recipient's bedside prior to transfusion of a unit of blood. Normally, the patient will have had an initial blood test using forward and reverse typing, performed by a blood bank. The unit of donor blood will also have been typed at the blood bank. Using the present apparatus, which employs forward blood typing of the whole blood sample, it will be possible, in almost all cases, to confirm the initial typing performed by the blood bank. In the rare case where the recipient patient's blood type as indicated by the apparatus test does not agree with the blood type indicated on the patient's chart, an additional verification test will be performed to correct any possible error prior to transfusion.

The advantages of the present invention include the ability to transport the apparatus to any location within a hospital or physician's office or elsewhere removed from a laboratory, and to carry out such blood typing tests in individual containers with predispensed blood typing reagents. Thus, any reasonably trained technician can perform quick, reliable blood typing tests. A determination of the patient's ABO blood group and Rh blood type by the physician as part of the patient's preliminary "work up" will also facilitate processing the patient for further treatment.

In accordance with the present invention, a portable blood testing apparatus may include a unitary assembly of microtubes, the number of microtubes being sufficient to constitute the number of reactions needed to determine an individual's ABO blood group. The invention may also include a reaction chamber assembly that is connected during use to the assembly of microtubes, forming an airtight seal with the microtube assembly.

Such a reaction chamber assembly may have a number of distinct reaction chambers containing blood typing reagents sufficient to determine the individuals ABO blood group. Each reaction chamber has a wall member which is made of a resilient portion which is deformed inwardly into the chamber by a removable element. During use, with the microtube assembly inserted into the reaction chamber assembly to form an airtight seal, the removable element is withdrawn from the reaction chamber assembly releasing the resilient portion of the chamber wall element. This movement creates a negative pressure in the presence of the airtight seal and causes the blood sample to flow from an individual microtube into the reaction chamber which contains a blood typing reagent.

The reaction chambers also preferably may have wall members that are constructed of optical enhancing materials "including a portion with magnifying properties" that enable rapid visualization of agglutination reactions. This reaction assembly may be labelled such that each reaction chamber is associated with an indicia indicating the blood typing reagent which is predispensed in that chamber. Advantageously both the microtube assembly and the reaction chamber assembly may be single use, disposable units.

Standard Rh blood typing requires the generation of heat for a short period of time. This test also requires the use of anti-Rho(D) reagent and an Rh control solution. Thus, another aspect of the present invention contemplates additional reaction chambers that contain blood typing reagents to perform Rh typing tests. At least one of these additional reaction chambers may include a hollow heating compartment formed between the inner and outer resilient portions of a wall member and which contains water and a chemical which reacts with the water to yield heat. An advantage of this aspect of the invention is that it provides a portable apparatus for determining the ABO blood group and Rh type in a location removed from a laboratory, such as the physician's office.

In almost all cases a preliminary determination using this invention will correctly identify the ABO blood group and Rh blood type of a patient. In the rare case where such an initial determination is inconsistent with an earlier, verification blood test or reverse typing, the inconsistency will be detected prior to any potentially life threatening treatment of the patient, such as transfusion.

It accordingly is an object of this invention to provide a portable blood testing apparatus to allow rapid determination of an individual's ABO blood group and Rh blood type at any location removed from a laboratory such as a hospital bedroom or physician's office.

Another object of this invention is to provide a portable apparatus that minimizes the possibility of introducing donor blood of an incompatible ABO blood group into a recipient by rapidly confirming the recipient's blood group before transfusion.

Still another object of this invention is to provide a portable blood testing apparatus that enables a technician to quickly and readily observe the results of the agglutination reactions.

Yet another object of this invention is to provide a method for rapidly determining an individual's ABO blood group and Rh blood type at any location removed from a laboratory. Other and further objects and advantages will appear hereinafter.

BRIEF DESCRIPTION OF THE DRAWINGS

FIG. 1 is a front elevational view showing the microtube assembly in the embodiment for determining ABO blood group;

FIG. 2 is a front elevational view of the reaction chamber assembly in the embodiment for determining ABO blood group;

FIG. 3 is a front elevational view of the microtube assembly connected to the reaction chamber assembly;

FIG. 4 is a cross-sectional view taken along line 4—4 of FIG. 3 and showing a single reaction chamber with the removable element present;

FIG. 6 is a front elevational view showing the reaction chamber assembly in the embodiment for determining ABO blood group and Rh blood type;

DETAILED DESCRIPTION OF THE PREFERRED EMBODIMENTS

Figure 5:
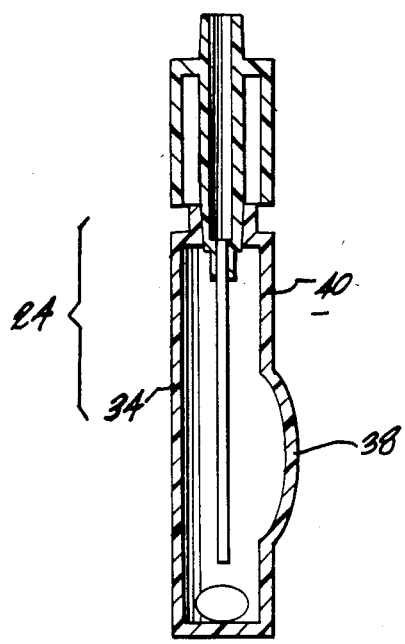
FIG. 5 is a cross-sectional view taken along line 4—4 of FIG. 3 and showing a single reaction chamber in expanded position with the removable element withdrawn.

Reference is now made to FIG. 1 of the drawing which specifically shows a blood collection or microtube assembly according to the present invention. The microtube assembly 10 is preferably molded as a single piece. The desired number of microtubes may be inserted during or after construction of the assembly. In the embodiment shown, three microtubes are illustrated, this being a sufficient number for performing the reactions to determine the ABO blood group of a specimen. The individual microtubes 12 of the unit are inserted into the tapering collar elements 14 and are joined together by the connecting element 16 which holds the microtubes in a linear arrangement. The tapering collar elements 14 are integrally attached to the connecting element 16. The microtube assembly 10 is also equipped with air vents 18 corresponding to the number of microtubes inserted, to enable the microtubes to be filled with a blood sample by capillary action. The entire assembly 10 may be sealed at the top with a strip of adhesive paper or plastic material 20 to prevent contamination.

A reaction chamber assembly 22 is illustrated in FIG. 2, and it is seen to be an elongated member with rectangular reaction chambers 24 joined in linear configuration and formed by wall members. In use, the apertures 26 in each chamber of the reaction chamber assembly 32 will fit tightly, but removably, around the tapering collar part 14 of the microtube unit 10 to form an airtight seal around the microtubes. FIG. 3 shows the microtube assembly 10 inserted into the reaction chamber assembly 22.

Continuing to refer to FIG. 2, the reaction chamber assembly 22 is provided with labels bearing markings or indicia 27 corresponding to the blood typing reagents contained in each of the reaction chamber units herein described. Thus, one wall member of each reaction chamber will bear a label printed with one of the following legends: anti-A; anti-B; anti-A,B; anti-Rho(D) and Rh control. These legends correspond to the blood typing reagents that are used in blood typing tests which contain antibodies to the known red blood cell antigens and are well known to those technicians who carry out such tests.

The reaction chamber assembly 22 is preferably molded as a single unit and is disposable. The desired number of reaction chambers are formed directly in the assembly. In the embodiment shown three reaction chambers are illustrated corresponding to the number of microtubes shown in FIG. 1 necessary to perform the usual tests to determine the ABO blood group of a specimen. The individual reaction chambes are formed with each sharing a common wall member 28 with the next in line. The reaction chambers may be of glass or plastic material, but as discussed below, in the preferred embodiment of the present invention the material preferably facilitates observation of the blood typing agglutination reactions.

The reaction chambers 24 each contain one of the following reagents; anti-A, anti-B, anti-A,B, anti-Rho(D) or Rh control. In the preferred embodiment such reagents have been dispensed into the reaction chambers in liquid form when the unit was formed. In another embodiment the reagent may have been dispensed in freeze-dried form. In addition, in the preferred embodiment, a portion 30 of the non-resilient wall member of each reaction chamber element is comprised of an optical-enhancing glass or plastic material. The optical-enhancing material may also be present as a portion of all wall members of each reaction chamber. The reaction chamber assembly 22 is also provided with an adhesive paper or plastic sealing element 32 to protect the enclosed predispensed reagents from contamination. In use the seal 32 is removed to allow insertion of the microtube assembly 10 into the apertures 26 of the reaction chamber assembly 22 as shown in FIG. 3.

Referring now to FIG. 4, each reaction chamber 24 is comprised of at least one wall member 34 made of hard, nonresilient material. Each reaction chamber 24 is also comprised of a resilient portion 38 of another wall member 40. In the preferred embodiment all reaction chambers 24 possess a resilient portion of a wall member at the same position such that a removable element 42 may be inserted into the reaction chamber assembly 22 during manufacture, deforming all the resilient portions of wall members in each reaction chamber along the same side of the apparatus. The removable element may be hard plastic or rubber material, or alternatively can be composed of a compressible material. Alternatively, one wall member of each reaction chamber could be made entirely of resilient material. The reaction chamber assembly 22 is also provided with an adhesive paper or plastic sealing element 43 to hold the removable element 42 in a position where it deforms the resilient portion 38 of wall member 40.

FIG. 5 shows a single reaction chamber 24 in expanded position. The resilient portion 38 of the wall member 40 has been released outward as a result of the removal of the removable element 42.

Referring now to FIG. 6, in the alternative embodiment of the invention to test for Rh blood type, there are two additional reaction chambers, 46 and 48 in the reaction chamber assembly 22.

Figure 7:
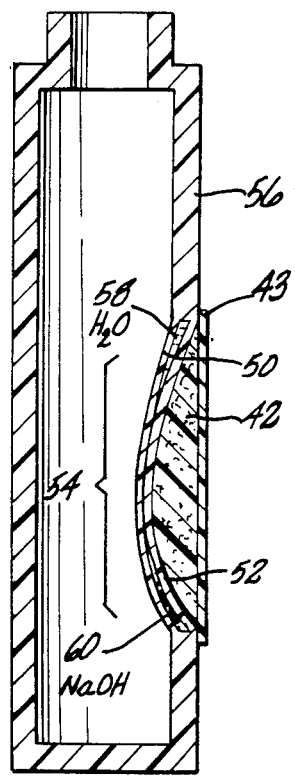
FIG. 7 is a cross-sectional view taken along line 7—7 of FIG. 6 and showing the heating compartment of a single reaction chamber with the removable element present in the embodiment for determining Rh blood type.
Figure 8:
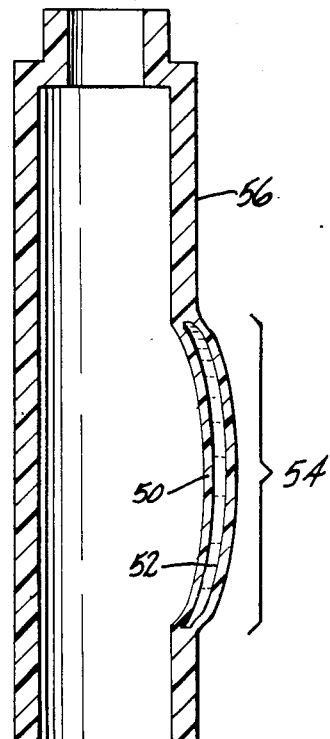
FIG. 8 is a cross-sectional view taken along line 7—7 of FIG. 6 and showing the heating compartment of a single reaction chamber in expanded position with the removable element removed, in the embodiment for determining Rh blood type.

Attention is now directed to FIG. 7 and 8. Each of the additional reaction chambers 46 and 48 is comprised of at least one inner resilient portion 50 of a wall member 56 and an outer resilient portion 52 of the wall member 56 forming a heating compartment 54. The remaining structure of each reaction chamber 46 and 48 is the same as that described above for FIG. 4. When the removable element 42 is inserted into the reaction chamber assembly 44 of this embodiment of the invention, both the inner, 50 and outer 52, resilient portions of the wall members are compressed together as shown in FIG. 7 so as to separate drops of water 58 at the apex of the heating compartment from the chemical that reacts with water to produce heat 60 at the base of the heating compartment.

FIG. 8 shows the heating compartment 54 with the removable element withdrawn; both the inner 50 and outer 52 resilient portions of the wall members are released expanding the reaction chamber and simultaneously opening the heating compartment so that the water 58 flows from the apex of the compartment into contact with the chemical 60 at the base of the compartment.

In use, a physician, nurse or technician will draw a sample of blood from a patient. The sealing material at the top of the microtube assembly will be removed and the microtubes of the microtube assembly will be placed onto the patient's blood sample, and drawn into the microtubes by capillary action. After removing the paper or plastic sealing material at the top of the reaction chamber assembly, the microtube assembly, will then be inserted into apertures in the reaction chamber assembly forming an airtight seal. Once inserted, the technician will withdraw the removable element so that the resilient walls of the reaction chambers will move outward, expanding the reaction chamber volume. This movement will create a negative pressure within the reaction chamber unit and the negative pressure will draw the blood from the microtubes into the reaction chambers containing the blood typing reagents.

The technician will gently shake the entire apparatus for a short period of time sufficient to mix the blood samples and reagents. After shaking, the technician will observe the contents of each reaction chamber by viewing through the optically enhanced wall member to determine whether or not agglutination had taken place in any chamber. It is not believed necessary to go into the details of the blood type group determination and the results of the test performed since this is well known to those having skill in the art, and is not part of this invention.

In the embodiment wherein the invention is used to determine the Rh blood type of a blood sample, the withdrawal of the removable element allows water droplets at the apex of the heating compartment to flow into the base of the heating compartment to come into contact with a chemical that reacts with water to produce heat, for example, sodium hydroxide. Thereafter, the mixture of water and chemical creates heat for a short period of time sufficient to facilitate the Rh typing agglutination reaction. Usually heat generated to a temperature of 40-°55° centigrade for 2-3 minutes will be sufficient. This embodiment also requires two additional reaction chambers with heating compartments which contain respectively the Rho(D) antigen and Rh control reagent.

After the tests are completed and read, the microtube assembly and the reaction chamber assembly may be discarded.

Thus, an apparatus and method for identifying a patient's ABO blood group and Rh blood type are disclosed. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A portable testing apparatus for determining a patient's ABO blood group using blood typing reagent agglutination reactions comprising:
   (a) a blood collection assembly having a plurality of microtubes for collecting the patient's blood sample;
   (b) a variable volume reaction chamber assembly for sealably receiving said blood collection assembly, including:
      (i) a plurality of reaction chambers formed by wall members to receive said microtubes;
      (ii) each of said reaction chambers having at least one nonresilient wall member;
      (iii) each of said reaction chambers having at least one resilient portion of a wall member; and
      (iv) a removable means abutting each of the reaction chambers so as to deform said reaction chambers inwardly at the resilient portion of the wall members, said removable means being held against said resilient portion of said wall members by a seal means.

2. An apparatus as defined in claim 1 wherein said reaction chambers are joined together in a linear configuration; said resilient portions of the wall members aligned along one side of the apparatus.

3. An apparatus according to claim 1 wherein said removable means consists of a compressible material.

4. An apparatus according to claim 1, wherein said removable means consists of a non-compressible material.

5. An apparatus according to claim 1 wherein said reaction chamber assembly receives the blood collection assembly so as to form an airtight seal between said blood collection assembly and said reaction chamber assembly.

6. An apparatus as defined in claim 5 wherein said airtight seal is formed by means for connecting said blood collection assembly to the reaction chamber assembly, said connecting means comprising:
   (a) a plurality of tapering collar elements integrally attached to said blood collection assembly into which said microtubes are inserted; and
   (b) apertures in each reaction chamber into which said tapering collar elements insert to form an airtight seal.

7. An apparatus as defined in claim 1 wherein said non-resilient wall members of said reaction chambers further include a portion with magnifying properties.

8. An apparatus as in claim 1, wherein said seal means is made of adhesive plastic or paper material.

9. An apparatus as in claim 1, further comprising blood typing reagents contained in liquid form in the interior of each of said reaction chambers.

10. An apparatus as in claim 1, further comprising blood typing reagents contained in freeze-dried form in the interior of each of said reaction chambers.

11. A portable testing apparatus for determining a patient's ABO blood group and Rh blood type using blood typing reagent agglutination reactions comprising:
   (a) a blood collection assembly having a plurality of microtubes for collecting the patient's blood sample;
   (b) a reaction chamber assembly for sealably receiving said blood collection assembly, including:
      (i) a plurality of reaction chambers formed by wall members to receive said microtubes;
      (ii) each of said reaction chambers having at least one non-resilient wall member;
      (iii) each of said reaction chambers having at least one resilient portion of a wall member, said resilient portion of the wall member of at least two reaction chambers having an inner resilient portion and an outer resilient portion, the inner and outer portions forming a heating compartment therebetween for catalyzing Rh typing reactions;
   (c) a chemical that produces heat when mixed with water contained at one end of said heating compartment; and
   (d) water contained at an opposite end of said heating compartment.

12. An apparatus as defined in claim 11 wherein said chemical is sodium hydroxide.

13. An apparatus according to claim 11, wherein said reaction chamber assembly receives the blood collection assembly so as to form an airtight seal between said blood collection assembly and said reaction chamber assembly.

14. An apparatus as defined in claim 11 wherein said apparatus further includes a removable means abutting each of the reaction chambers so as to deform each reaction chamber inwardly at the resilient portion of a wall member.

15. A method for determining a patient's ABO and Rh blood type, comprising the steps of:
   (a) obtaining a blood sample from the patient;
   (b) filling a plurality of microtubes with the blood sample by contacting the tubes to the patient's blood;
   (c) connecting said microtubes to a reaction chamber assembly wherein said reaction chamber assembly includes:
      (i) a plurality of reaction chambers formed by wall members;
      (ii) each of said reaction chamber having at least one resilient portion of a wall member, and said resilient portion of the wall member of at least two reaction chambers having an inner resilient portion and an outer resilient portion, the inner and outer portions forming a heating compartment therebetween;
      (iii) a chemical that produces heat when mixed with water contained at one end of said heating compartment;
      (iv) water contained at an opposite end of said heating compartment;
      (v) a removable means abutting each of the reaction chambers so as to deform said reaction chambers inwardly at the resilient portions and form said one end and said opposite end;
   (d) causing the blood sample to flow from the microtubes into the plurality of reaction chambers;
   (e) mixing said blood samples and blood typing reagents in said reaction chambers;
   (f) heating the mixture of blood sample and Rh blood typing reagents in said reaction chambers;
   (g) observing said mixtures in the reaction chambers for agglutination;

Wherein said step of causing the blood sample to flow from the microtubes and said step of heating the mixture of blood sample and Rh blood typing reagents comprises removing said removable means to generate a negative pressure within the reaction chamber and to increase the volume of said heating compartment and simultaneously allow the water to contact the chemical within the heating compartment.

16. The method according to claim 15, wherein said step of connecting includes the step of inserting said microtubes into said reaction chamber assembly to form an airtight seal.

17. A method as in claim 15 wherein said step of heating further includes wating for said water and chemical reaction to heat said Rh typing reagents to a temperature between 40 degrees to 55 degrees centigrade.

18. A method as in claim 17 wherein said water and chemical reaction is allowed to continue for 2-3 minutes prior to the step of observing said mixtures for agglutination.

* * * * *